| United States Patent [19] | [11] Patent Number: 5,037,924 |
| Tazi et al. | [45] Date of Patent: Aug. 6, 1991 |

[54] DENTURE ADHESIVE

[75] Inventors: Mohammed Tazi, Wayne; Robert B. Login, Oakland, both of N.J.; Yoon T. Kwak, Brooklyn, N.Y.; Balgopal Gangadharan, Caldwell; Rama K. Haldar, Randolph, both of N.J.

[73] Assignee: GAF Chemicals Corporation, Wayne, N.J.

[21] Appl. No.: 557,356

[22] Filed: Jul. 25, 1990

[51] Int. Cl.$^5$ ............... C08F 222/06; C08F 216/12; C08F 210/10; C08L 35/08; C08K 5/09

[52] U.S. Cl. ..................... 526/272; 526/332; 526/348.7; 323/118; 524/400

[58] Field of Search .............. 526/272; 523/118; 524/400

[56] References Cited

U.S. PATENT DOCUMENTS 3,984,574 10/1976 Comollo ........................ 426/4
4,318,742 3/1982 Lokken ........................ 106/35
4,506,041 3/1985 Tanigawa et al. ............... 523/139
4,910,247 3/1990 Haldar et al. .................. 524/400

FOREIGN PATENT DOCUMENTS 5968392 4/1984 Japan .

Primary Examiner—Joseph L. Schofer
Assistant Examiner—Wu C. Cheng
Attorney, Agent, or Firm—Walter Katz; Marilyn J. Maue; Joshua J. Ward

[57] ABSTRACT

According to this invention, there is provided a denture adhesive which is a mixed partial salt of a terpolymer of maleic anhydride, (MA) a $C_1$-$C_4$ alkyl vinyl ether (AVE) and isobutylene (IB) vinyl ether, having a weight average molecular weight of about 30,000 to 400,000, preferably about 50,000 to 350,000. The terpolymer has its components in the molar ratio of MA:AVE:IB of about 1:0.4–0.9:0.1–0.6, preferably about 1:0.5–0.8:0.2–0.5.

18 Claims, 1 Drawing Sheet

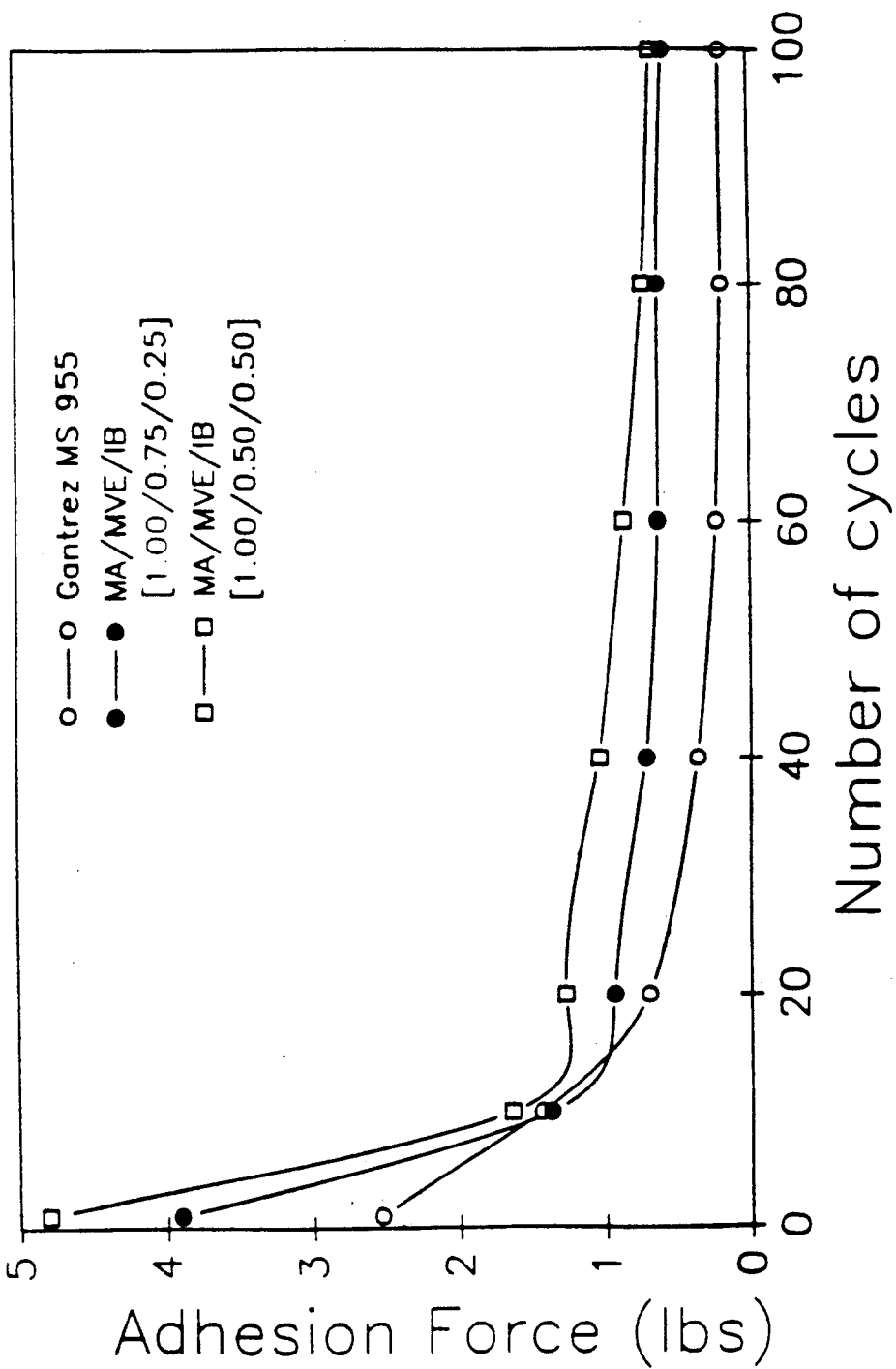

DENTURE ADHESIVE

BACKGROUND OF THE INVENTION

1. Field of the Invention

This invention relates to denture adhesives of mixed partial salts of terpolymers of maleic anhydride, a $C_1$-$C_4$ alkyl vinyl ether and isobutylene, and particularly to denture adhesive compositions thereof.

2. Description of the Prior Art

Various adhesive compositions have been employed for fixing dentures. U.S. patents disclosing such compositions include U.S. Pat. Nos. 3,003,988; 3,736,274; 3,740,361; 3,833,518; 3,868,339; 3,868,432; 4,183,914; 4,217,342; 4,217,343; 4,521,551 and 4,758,630. Such denture adhesive compositions, however, are found to be effective for only a limited time of up to 8 hours and some for as little as 2 or 3 hours.

Accordingly, it is an object of this invention to provide a denture adhesive composition having both initial stick force strength and long term performance characterized by prolonged adhesion properties.

Another object herein is to provide a mixed partial salt of maleic anhydride-$C_1$-$C_4$ alkyl vinyl ether-isobutylene terpolymer having effective strength properties for use as a denture adhesive.

These and other objects and features of the invention will be made apparent from the following disclosure and description.

DESCRIPTION OF THE DRAWING

The FIGURE is a graph of adhesive force in lbs. vs. number of cycles during Instron testing of adhesive compositions of the invention.

SUMMARY OF THE INVENTION

According to this invention, there is provided a denture adhesive which is a mixed partial salt of a terpolymer of maleic anhydride (MA), a $C_1$-$C_4$ alkyl vinyl ether (AVE) and isobutylene (IB) having a weight average molecular weight of about 30,000 to 400,000, preferably about 50,000 to 350,000.

The terpolymer suitably has its components in the molar ratio of MA:AVE:IB of about 1:0.4-0.9:0.1-0.6, preferably about 1:0.5-0.8:0.2-0.5.

The partial mixed salts include calcium/sodium salts wherein the equivalent ratio of calcium to sodium cations may range from 2:1 to 10:1, preferably between 3:1 to 7:1, and the degree of neutralization of initial carboxyl groups is from 0.5 to 0.95, preferably from 0.7 to 0.9.

DETAILED DESCRIPTION OF THE INVENTION

The terpolymer of the invention is made by polymerizing the monomers in the presence of a free radical initiator, at about 50° to 150° C., and usually about 60° to 80° C. Suitably, polymerization can be carried out in a solvent, such as toluene or benzene, although preferably, a cosolvent system is used which comprises about 5 to 80 percent by weight, preferably 10 to 75 percent, of ethyl acetate, and about 20 to 95 percent by weight, preferably 25 to 90 percent by weight, of an aliphatic or cycloaliphatic hydrocarbon having a boiling point of at least 10° C. above the reaction temperature, and which is preferably cyclohexane. In this cosolvent system, a pumpable slurry of the copolymer in the cosolvent is produced, from which the copolymer can be recovered readily as a uniform, fine white powder having substantially no residual maleic anhydride.

The adhesive copolymer of this invention is converted to its mixed partial salt, which preferably is employed as a dry powder having a particle size of less than 250μ, and, more desirably, a particle size of from about 5 to about 200μ.

Denture adhesive compositions are provided herein by incorporating dry powders of the above adhesive copolymer as mixed salts into a liquid base carrier by mixing until a homogeneous cream paste suspension or collodial dispersion is obtained, usually within a period of from about 20 minutes to about 5 hours. The resulting composition contains an effective adhesive amount of the adhesive copolymer mixed salt, generally between about 5 and about 50 wt. %, and preferably between about 10 and about 35 wt. %, of the final composition.

Suitable mixed partial salts herein include the calcium/sodium mixed partial salts which are prepared by reacting the copolymer with suitable bases. Preferably the equivalent ratio of calcium cations to sodium cations in the mixed partial salts may range from 2:1 to 10:1 and most preferably is between 3:1 and 7:1 (on a mole ratio basis, the range of calcium to sodium cations is from 1:1 to 5:1, most preferably from 1.5:1 to 3.5:1). The sum total of cations in the mixed partial salt should be sufficient to give a degree of neutralization of from 0.5 to 0.95 and preferably 0.7 to 0.9 of the total initial carboxyl groups in the copolymer. In the determination of the total initial carboxyl groups in the copolymer, the anhydride radical is considered as containing 2 initial carboxyl groups.

The base carrier portion of the composition generally includes a water soluble or partially water soluble hydrophilic carrier which is capable of swelling upon exposure to moisture to form a mucilaginous mass. Such carrier materials include natural and synthetic gums, viscous liquids, gels and powders. Among those suitably employed as base carriers in the composition are karaya gum, gelatine, gum tragacanth, gum acacia, gum shiraz, algin, sodium alginate, tragacanth, methyl cellulose, a mixture of petrolatum and mineral oil, glycerine, polyvinylpyrrolidone, K-30 and K-90, carboxymethyl cellulose, ethylene oxide polymers, of which the preferred is a mixture of petrolatum and mineral oil in a ratio of 40:60-60:40.

The adhesive copolymer of the invention can be employed as the sole adhesive component in the denture adhesive composition or it can be used as a coadhesive with another adhesive material. Such adhesive additive, if present, will generally comprise about 5-20% by weight of the composition. Suitable adhesive additives include natural or synthetic polymers such as cellulose, karaya gum, gum tragacanth, gum acacia, carboxymethyl cellulose or salt thereof, polymethacrylate, polyvinylpyrrolidone, polyvinyl acetate, or any mixture of the above.

The compositions of the invention are particularly useful for affixing dentures and can also be used in surgical procedures which require temporary displacement of tissue. As a denture adhesive, the thermal stability of the present composition, over a temperature range which is at least sufficient to embrace all conditions encountered by living tissue, e.g. 5°-50° C., is particularly desirable. Because of their increased adhesive strength and thermal stability, the composition retains its adhesive properties over a long period of time, i.e. up to 24 hours.

The following illustrates a few representative formulations into which the adhesive copolymer can be added in effective amounts up to about 50%.

|  | Wt. % |
|---|---|
| Cream Denture Adhesive Composition | |
| Mineral Oil | 30 |
| Petrolatum | 25 |
| Sodium carboxymethyl cellulose (adhesive additive) | 20 |
| Colorant | 1 |
| Flavoring Agent | 0.5 |
| Material of Invention | 23.5 |
| Paste Ostomy Adhesive Composition | |
| Mineral oil (heavy) | 35 |
| Glycerine | 5 |
| Polyvinylpyrrolidone | 20 |
| Carboxymethyl cellulose | 5 |
| Tosylate of quat. amino-N-propylpyrrolidone | 0.5 |
| Matrial of Invention | 34.5 |
| Denture Adhesive Powder Composition | |
| Gum tragacanth | 40 |
| Gum acacia | 20 |
| Spearmint oil | 0.05 |
| Material of Invention | 39.05 |

Reference is now made to the following examples which provide preferred embodiments of the invention.

EXAMPLE 1

PREPARATION OF TERPOLYMER

A 1-liter resin kettle was equipped with a stirrer, reflux condenser, a $N_2$ inlet tube and an inlet closed with a rubber septum for introduction of a polymerization initiator. The kettle was charged with 60.0 g. (0.61 mole) of maleic anhydride (MA), 97.9 g. (50 wt. %) of ethyl acetate (EA) and 97.9 g. (50 wt. %) of cyclohexane (CH). Agitation of the mixture at 180 rpm was begun, and the system was purged by bubbling in $N_2$ for 30 minutes, during which time the maleic anhydride dissolved completely. The reaction mixture was then warmed to 58° C. and 0.2 g. of Lupersol 11 (Pennwalt) was injected through the septum to initiate polymerization. Simultaneously, dropwise addition of 19.6 g. (0.33 mole) of methyl vinyl ether (MVE) and 18.88 g. (0.33 mole) of isobutylene (IB) was begun and continued over a period of 3 hours. Lupersol 11 was added in an amount of 0.4 g. after 1½ hours. After completion of all additions, which required 58° C., the resulting mixture was maintained at 58° C. for 1½ hours. Thereafter, the reaction mixture was cooled to room temperature, excess MVE vented and the slurry was pumped out of the kettle into a filtration unit. There the slurry was filtered and the polymer product was dried for about 12 hours at 65° C. in a forced air oven. The polymer product was a uniform, fine white powder, having a molar ratio of MA:MVE:IB of 1:0.55:0.55.

EXAMPLE 2

The procedure of Example 1 was followed to provide copolymers of varying compositions within the molar range of 1:0.4–0.9:0.1–0.6, including one at 1.0:0.75:0.25.

EXAMPLE 3

PREPARATION OF DENTURE ADHESIVE COMPOSITIONS OF INVENTION

The terpolymers of Examples 1-2 were converted to their mixed, partial salts illustrated as follows: 58.6 g. of the terpolymer was charged into a 250 ml round bottom, 3-necked flask together with 260 g. of isopropyl alcohol. The contents were agitated to make a slurry and 18.1 g. of calcium hydroxide was added slowly with agitation during 15 minutes. Then 2.85 g. of sodium hydroxide dissolved in 112.5 g. of water was added with agitation. The mixture was heated at 45° C. with agitation for 4½ hours. The pH of the liquid phase was 6.1. The mixture was filtered and the precipitate was dried in a vacuum oven overnight at 65° C. to provide 93.4 g. of a dried product. Similar copolymer conversions to the mixed partial salts were effected for the terpolymers of Example 2.

EXAMPLE 4

PREPARATION OF ADHESIVE COMPOSITIONS FOR INSTRON TESTING

The dry, mixed salt of the MA/MVE/IB terpolymer of Example 1 was milled to pass through a number 60 mesh sieve (250 u) and the resulting powder was then dispersed at a temperature of 55°–65° C., followed by cooling to 20°–25° C., into a petrolatum base using mechanical stirring. The ratio of copolymer to base by weight was 1:2. The resulting cream dispersion was collected as the desired adhesive composition.

EXAMPLE 5

Adhesive compositions of GANTREZ MS-955, which is a commercial mixed salt copolymer of maleic anhydride and methyl vinyl ether, also were prepared for testing in the same manner as described above for Examples 1-2.

EXAMPLE 6

EVALUATION OF DENTURE ADHESIVE COMPOSITIONS 2 g. samples of each of the above prepared compositions were evaluated for adhesion characteristics by Instron testing according to the following procedure:

In the first step, the upper and lower plates of the Instron apparatus were brought together to obtain a zero position. The upper plate was then raised 0.06 inch and the upper cycle limit on the Instron indicator is set at this point. The upper plate was then lowered and the lower cycle limit was set. In its lowest position, the upper plate was distanced 0.03 inch above the lower plate.

With these Instron settings determined, the upper plate was then raised and 2 g. of the test sample was uniformly spread over the surface of the lower plate in a 1/16 to ⅛ inch thickness; thereafter simulated salivary fluid was applied over the sample so that it was barely covered.

The Instron crosshead was cycled between the previously set limits at a crosshead speed of 0.2 in./min. The Instron chart was set in the continuous mode at a speed of 2 in./min. to record the compression and adhesion force for each cycle, 5 to 100 cycles.

At the end of 100 cycles, the motion of the upper plate was halted and raised high enough to clean the surface before the next adhesive test.

Each recording was analyzed and the adhesional forces (lbs.) for the 1st, 5th, 10th, 20th, 40th . . . 100th cycles were recorded and then plotted graphically.

The results of this study are shown in the FIGURE which data show that significantly better initial stick strength and long term adhesion is obtained for adhesive formulations containing the terpolymer compositions of the invention as compared to a related copolymer composition (MS-955), which is considered useful as a denture adhesive.

While the invention has been described with particular reference to certain embodiments thereof, it will be understood that changes and modifications may be made which are within the skill of the art. Accordingly, it is intended to be bound only by the following claims, in which:

What is claimed is:

1. A denture adhesive which comprises a mixed, partial calcium/sodium salt of a terpolymer of maleic anhydride, a $C_1$-$C_4$ alkyl vinyl ether and isobutylene, said terpolymer having a weight average molecular weight of about 30,000 to 400,000, and being in the molar ratio of about 1:0.4–0.9:0.1–0.6, respectively.

2. A denture adhesive according to claim 1 wherein said terpolymer is in the molar ratio of about 1:0.5–0.8:0.2–0.5.

3. A denture adhesive composition according to claim 2 wherein said terpolymer has a molecular weight of about 50,000 to 350,000.

4. A denture adhesive according to claim 1 wherein said alkyl vinyl ether is methyl vinyl ether.

5. A denture adhesive according to claim 1 wherein the calcium to sodium cation equivalent ratio is 2:1 to 10:1.

6. A denture adhesive according to claim 5 wherein said molar ratio is 1:0.5:0.5.

7. A denture adhesive according to claim 5 wherein said molar ratio is 1:0.75:0.25.

8. A denture adhesive according to claim 1 wherein the sum total of cations in the mixed partial salt is sufficient to give a degree of neutralization of from 0.5 to 0.95 of the total initial carboxyl groups in the copolymer.

9. A denture adhesive according to claim 8 wherein said sum total is 0.7 to 0.9.

10. A denture adhesive composition comprising an effective adhesive producing amount of the adhesive terpolymer of claim 1 and a base carrier.

11. A composition according to claim 10 wherein the adhesive terpolymer is present in a concentration of about 5 to 50 weight percent of the composition.

12. A composition according to claim 10 which includes about 5 to 20% by weight of an adhesive additive which is a natural or synthetic polymer.

13. A composition according to claim 12 wherein said polymer adhesive additive is karaya gum or carboxymethyl cellulose.

14. A composition according to claim 10 wherein said base carrier is a water soluble or partially water soluble hydrophilic carrier capable of swelling upon exposure to water to form a mucilaginous mass.

15. A denture adhesive composition according to claim 10 wherein the calcium to sodium cation equivalent ratio is 2:1 to 10:1.

16. A denture adhesive composition according to claim 10 wherein the ratio is 3:1 to 7:1.

17. A denture adhesive composition according to claim 10 wherein the sum total of cations in the mixed partial salt is sufficient to give a degree of neutralization of from 0.5 to 0.95 of the total initial carboxyl groups in the terpolymer.

18. A denture adhesive composition according to claim 17 wherein said sum total is 0.7 to 0.9.

* * * * *